United States Patent [19]

Young et al.

[11] Patent Number: 5,039,247
[45] Date of Patent: Aug. 13, 1991

[54] ADJUSTABLE HINGE DEVICE

[75] Inventors: David E. Young, Watlington; Kenneth P. Davis, Hillington, both of England

[73] Assignee: Protectair Limited, Abingdon, England

[21] Appl. No.: 427,010

[22] Filed: Oct. 25, 1989

[30] Foreign Application Priority Data

Oct. 26, 1988 [GB] United Kingdom ............... 8825001

[51] Int. Cl.⁵ .................................. A61F 3/00
[52] U.S. Cl. .................................. 403/92; 403/62;
403/84; 403/113; 128/80 C; 128/80 F
[58] Field of Search .................. 403/62, 84, 92, 96,
403/80, 113, 117; 128/80 C, 80 F, 88

[56] References Cited

U.S. PATENT DOCUMENTS

| | | | |
|---|---|---|---|
| 3,046,799 | 7/1962 | Ash, II et al. | 403/62 X |
| 3,779,654 | 12/1973 | Horne | 403/62 |
| 4,249,524 | 2/1981 | Anderson | 128/80 C |
| 4,337,764 | 7/1982 | Lerman | 128/80 F |
| 4,520,802 | 6/1985 | Mercer et al. | 128/80 C |
| 4,599,998 | 7/1986 | Castillo | 403/84 X |
| 4,620,532 | 11/1986 | Houswerth | 128/80 C |
| 4,777,941 | 10/1988 | Borig et al. | 128/80 C |

FOREIGN PATENT DOCUMENTS

| | | | |
|---|---|---|---|
| 38412 | 10/1906 | France | 403/62 |
| 2182714 | 5/1987 | United Kingdom. | |
| 82/02658 | 8/1982 | World Int. Prop. O. . | |

Primary Examiner—Randolph A. Reese
Assistant Examiner—Franco S. De Liguori
Attorney, Agent, or Firm—Tilton, Fallon, Lungmus

[57] ABSTRACT

An orthopedic and orthotic hinge having a hinge body that includes two spaced, parallel plates with two hinge arm carriers having end portions pivotally mounted between the plates for movement in directions of flexion and extension. The end portions of the hinge arm carriers have peripheral teeth that respectively engage two toothed slide members. Such members are slidably disposed between the plates, preferably carried in grooves formed therein, and are independently movable with respect to each other when the hinge arm carriers are pivoted. First and second variable stops are provided by the hinge for limiting the extent of sliding movement in opposite directions of the two slide members, thereby restricting extension and flexion of the hinge arm carriers while at the same time permitting true bi-pivotal operation of the hinge. In one embodiment, the variable stops are offset from the midplane of the hinge body and the toothed slide members have extensions engageable with such stops.

7 Claims, 5 Drawing Sheets

ADJUSTABLE HINGE DEVICE

This invention relates generally to adjustable hinges and more especially to bi-pivotal orthopaedic and orthotic hinge mechanisms which are used in braces of various kinds.

Orthopaedic and orthotic hinges vary considerably in design and function. They are employed at joints, such as the knee and elbow and their function is usually to supplement or partially substitute for the weight-bearing and motional characteristics of these joints. They are generally used in pairs with one hinge fitted laterally and the other fitted medially across the joint.

Orthopaedic and orthotic hinges are of two main types. The first employs a single pivot and is generally described as uniaxial or unipivotal; this type is quite commonly used in knee braces fitted in the practice of sports medicine, often following damage to the ligaments of the knee.

Uniaxial hinges are commonly fitted to heel cups. This is a common name applied to the terminal element in a cast brace. More recently, uniaxial hinges have been used in lower leg walking devices for fractures of the foot. These devices are used instead of short leg walking casts.

In regard to the knee, single pivot hinges are unphysiological because the biomechanics of the knee are fundamentally different and it does not move in the same way.

The second type of hinge mechanism has a central mount or plate which bears two pivots. The hinge arms are mounted, one on each pivot and each arm has gear teeth at its extreme end such that the teeth mesh with those of its neighbour. The effect of this is that when one hinge arm is moved, the other hinge arm must move also. This type is very widely used in cast bracing hinges and knee braces.

In mechanical terms a geared two pivot mechanism loses one degree of freedom when compared with two pivots which are not geared together. Geared two pivot hinges are also unphysiological when used at the knee because they effectively offer a single pivot point which migrates backwards when the hinge is moved from the fully extended to the fully flexed condition. In commercially available types, this migration is about 8 mm.

Knee motion involves gliding of the femoral condyles over the tibial plateau as the knee extends from the fully flexed position. As the knee moves into the last 20 degrees or so of extension, a marked pivotal element is introduced between the tibia and femoral condyles and over the last 5 or so degrees of extension there is a rotational "screw-home" component which occurs about a substantially vertical axis.

The third less common type of orthopaedic hinge does offer good tracking of the human knee joint. It employs two truly independent pivots each in conjunction with a stop incorporated in the body to prevent hyperextension. This type of hinge is called a true bi-pivotal hinge or by some authors a true bi-axial hinge.

Very few commercially available examples of true bi-pivotal hinges are known to the present inventors.

One, a sports brace made by Omni Scientific of Martinez, Calif., is believed to be based on U.S. Pat. No. 4,249,524 and a PCT publication WO 82/02658 in the name of Anderson.

This U.S. patent teaches a bi-pivotal hinge which appears to have unphysiological characteristics. The pivots are very widely spaced and shortening could occur in the hinge as it flexes, leading to effective shortening of the cast or brace in which it is used. This allows the knee joint or limb to "piston" which is undesirable, especially in a damaged knee, in a knee which has recently undergone surgical repair or in a leg where there is a fracture.

The hinge illustrated in Anderson's PCT publication is different insofar as the termination are concerned. However, judging from the drawings the pivots are still widely separated.

In effect, the hinge centre bar of the hinge described in the U.S. patent fulfils the function o both a mounting for the pivots and of hinge arms it extends as far as the members normally regarded headplates. In the PCT publication, the hinge bar appears to extend quite close to the headplates.

This suggests that Anderson may have understood neither the significance of pivotal spacing in regard to "pistoning" nor that wide spacing will detract from proper function of a hinge incorporated in a brace. For instance, where wide pivotal spacing is employed, the medial collateral ligament will receive little, if any, protection from a brace should the knee receive a lateral blow during contact sports when the joint is in a moderately flexed position.

Although Anderson briefly mentions stops in the PCT publication, he does not describe a variable motion limiting system. In any true bi-pivotal hinge, the interrelationship between the control of motion and the pivot spacing is important.

In U.S. Pat. No. 4,337,764 Lerman describes an adjustment mechanism for two-pivot geared hinges. The system depends on a hinge backplate with an arcuate slot in which are located two compression screw sets lying outside either side of the hinge arm. In commercially available versions of this device, such as those hinges supplied in the U.S.A. by United States Manufacturing Company of Pasadena, Calif., there are two such slots and a total of four compression screw sets.

Lerman's U.S. patent does not read for bi-pivotal hinges as it calls for the hinge arms, which he calls first and second bars, to be provided with pivot means so that they may move relative to one another. Lerman achieves this by providing the bars with gear teeth which mutually enmesh so that when one bar is moved, the other must also move. In a true bi-pivotal hinge, the pivots are independent.

Tests which have been carried out using an Instron machine, show that the Lerman stop mechanism is liable to slip at physiological loads and that this slippage occurs in an unpredictable manner.

In 1983, Protectair Limited of Abingdon, Oxfordshire introduced into the European marketplace a true bi-pivotal hinge with closely spaced pivots, under the name Sheffield System. It features a hinge body with a metal chassis having arcuate slots at each end.

Compression screws, fitted with washers and nuts, lie in the slots and the positions of the compression screw sets may be varied over a wide range. Unlike the Lerman hinge, the compression screws do not act against either side of the hinge arms, instead they abut a pin rivetted to each hinge arm centrally under the arcuate slots. Like the Lerman hinge adjustment mechanism, this system has also been found to slip on Instron testing at physiological loads. However, when accessory locking plates supplied for use with this design, were fitted, slippage could not be demonstrated.

In co-pending British Patent Application Publication Number 2182714, there is described a true bi-pivotal knee hinge which employs closely spaced pivots. This device is also made by Protectair Limited, Abingdon, Oxfordshire and has been sold under the names "Adjustalok" R and "Locking Knee Cast Hinge" R.

In this device, first and second hinge arm carriers are mounted in first and second closely spaced pivots. Each hinge arm carrier has two cam abutment stopsarising from it, one either side of and close to its pivot. Motion limiting screws, one to control flexion, the other to control extension, are provided for each pivot. This arrangement is a deadstop mechanism and unlike either the Lerman system and the Sheffield System, it has been shown to withstand slippage at loads well above the physiological maximum.

The system is compact and is ideal for many applications including cast bracing hinges and most especially for incorporation into a post-operative brace for limiting knee motion immediately following ligament reconstruction surgery.

It has been confirmed, by means of combined video, computer and force plate gait analysis, that these bi-pivotal hinges with closely spaced pivots, when used at the knee, introduce less disturbance to the normal gait (or walking pattern), than either geared two-pivot hinges or single axis hinges.

Furthermore, it has been confirmed at Sheffield and Brunel Universities, that with the spacing of the pivots used in these bi-pivotal hinges, the variable instant centre pathway of the knee during the flexion/extension cycle can be almost entirely accommodated in the majority of adults. The instant centre pathway of the knee is the locus of the effective knee axis as the knee joint moves through a complete cycle of flexion and extension.

Also, pistoning does not occur in such hinges as it does in those described above when the knee is under load (provided the hinges are fitted properly). This work was carried out at Derby Royal Infirmary, Derby, United Kingdom in 1984 and was presented at the International Orthopaedic Association meeting in Washington D.C., U.S.A. 4th–10th May 1987 by Dr David Pratt. Dr Pratt's principal co-author was Mr David Rowley M.D., F.R.C.S.

U.S. Pat. No. 4,520,802 granted to Mercer and Aaserude teaches another bi-pivotal hinge featuring wide pivot spacing. These authors' principal disclosure is, however, their motion control system based on indexing blocks. The system they describe is discontinuous and leaves the user subject to the values on the index blocks made available by the manufacturer. Furthermore, the time taken to remove parts of the device and to select and substitute accessories would be considerable and not appropriate to busy clinics and doctors' offices where there is usually the need to process numerous patients efficiently and quickly. As taught, the intention seems primarily to provide flexion control.

Most hinges have securing means for fixing them directly or indirectly to a limb. Nowadays there is an increasing trend towards the use of devices which are retained on the limb by means of several straps. Where this method is employed, the hinge mechanism will usually have arms fitted with curved plates which are often called shells.

Where the hinge mechanism is to be retained on the limb by a cast, it will usually have hinge arms which terminate in structures adapted for embedding in the cast and frequently termed headplates or anchor plates.

Orthotic hinges are normally supplied as independent units which are subsequently either built directly onto plastics orthoses or fitted to mating side arms called "steels" and then incorporated into calipers. Lower limb orthoses in particular are generally secured to the limb with straps.

Observations made under widely varying conditions in several different countries have led to the conclusion that strap-on devices have more potential for relative motion between the limb and the device than do casts. This is primarily because casts are inherently rigid and constitute a fully circumferential integrated structural unit, whereas strap-on devices are usually made from a combination of soft goods and flexible materials and cannot form an integrated circumferential structure.

It is important to understand, therefore, that in the design of motion control mechanisms for orthopaedic and orthotic hinges, adjustment systems should be capable of continuous variation. This ensures that proper compensation for relative motion between the leg and the brace when such hinges are used with strap-on braces, can be achieved.

Many authors have described means for limiting motion in orthopaedic hinges but all too frequently the type of hinge selected in the first place is unsuitable for the joint being braced, especially when complex motion is involved such as that of the knee joint.

Consequently, although the motion control mechanism described for a "conventional" leg brace in U.S. Pat. No. 4,620,586 is clever and compact, the uniaxial hinge is not very suitable for knee bracing applications since no uniaxial hinge can ever track the human knee satisfactorily. If the brace in which the hinge is incorporated fits snugly, such a hinge will impart undesirable forces to the joint.

Similarly, in U.S. Pat. No. 4,599,998, the motion control system described based on a ratchet system is compact and neat but it is applied to a geared two pivot system which again does not tract the human knee very well.

A different type of adjustment mechanism for a two-pivot geared hinge is used in a design supplied by Rolyan Manufacturing Co Inc of Menomonee Falls, Wis., U.S.A. In this device, two screws located in the top of the hinge body are used to limit travel of one hinge arm in flexion and extension respectively. This is achieved by driving the screws down into the body so that the ends strike the top edges of the hinge arms.

The screws remain exposed at all times and require a locking nut to maintain adjustment. The hinge may be free or locked in one position or set for limited ranges of motion.

The bi-pivotal hinge recently sold by Seton Products Ltd (Sepro in the U.S.A.) under the name Polymotion, is bi-pivotal and has abutment stops on hinge arm carriers for both flexion and extension. These are curved and drive against cam adjusters. This hinge seems to yield from a set position at relatively low loads.

In the damaged but developmentally normal knee great attention to accurate tracking is necessary, since, with well managed rehabilitation, very good results can be obtained. However, with grossly abnormal knees ravaged either by disease or birth defect and in which there is no hope of normal motion, most professionals have, up to now, employed a less complex uniaxial hinge and other factors in the design of the device, such as locking mechanisms have been regarded as more important. This approach may not be justified.

The present invention now provides a close coupled bi-pivotal hinge for the knee in applications such as functional braces and calipers.

More particularly, the present invention seeks to provide a hinge mechanism for use in braces and orthotic devices with a first set of stops to block extension in a continuously variable manner over a useful clinical range by means of a single adjuster, a second set of stops to block flexion in a continuously variable manner over a useful clinical range by means of a single adjuster, and extension and flexion blocking in the hinge without risk of loss of adjustment at maximal physiological loads.

In accordance with the invention, there is provided an orthopaedic and orthotic hinge comprising a faceplate and a backplate in spaced parallel relationship;

first and second pivot means in the form of axial bearings between and in a plane normal to the faceplate and backplate;

first and second hinge arms or hinge arm carriers borne on the axial bearings and having peripheral teeth which engage first and second slide members, respectively, the slide members being in mutual sliding contact and independently movable; and first and second variable stops adapted to limit the anterior and posterior movement of both slide members and thereby restrict extension and flexion of the hinge arms or hinge arm carriers.

The principal components of a preferred hinge according to the invention are a hinge body with two spaced, parallel plates that may be designated as a faceplate and backplate, two hinge arm carriers or saddles each having a plurality of teeth around their ends which face in towards the mid-line of the hinge body and two toothed slide members one engaging the first hinge arm teeth, the other engaging the second hinge arm teeth. The toothed slides fit back to back against one another and are nested into the hinge body in grooves in the backplate and faceplate. Screw adjusters are housed at the top and the bottom of the hinge body in bosses.

The hinge body components may be made of metal, plastics or composite materials. Holes in the faceplate accept inserts which form journals or axles or pivots for the hinge arms. The backplate is similar in appearance to the faceplate and these two components are essentially parallel. Holes in the backplate line up with the holes in the faceplate and accept the inserts. These in turn are provided with securing means, such as threads, which enable the elements of the hinge mechanism to be retained in place.

The hinge arms may also be made from a variety of materials. The ends of the hinge arms are fitted into carriers called saddles which are conveniently stainless steel castings in low profile versions and conveniently of plastics in full thickness designs. These extend beyond and between the pivots where their ends are formed into teeth. The saddles locate between the faceplate and backplate as a firm fit with minimal side-play.

Each saddle has a bearing hole near the end which is a close fit over one pivot. The teeth on each saddle enmesh with corresponding teeth on the short vertical toothed slides. The slides are mounted back to back within the hinge body and each has a rectangular lug on either side. These engage grooves in the faceplate and backplate in which they can thus slide up and down whilst being retained. Bosses formed at the top and bottom of the hinge in the faceplate, backplate or combined structure house a substantial threaded adjustment screw which protrudes into the hinge body and impinges on the top and bottom surfaces, respectively of each of the toothed slides. The screw adjusters thus act as continuously variable abutment stops against which each toothed slide ma impinge. The other end of each hinge arm is suitably adapted to fit a headplate, brace or orthosis as required.

It will be appreciated that each adjusting screw relates to two abutment stops, one on each rack. The posterior screw adjuster may be turned clockwise causing extension of the hinge to be blocked in a continuously variable manner. Similarly, the anterior screw adjuster may be turned clockwise blocking flexion of the hinge. The mechanism is so constructed that these adjustments extend over at least a useful clinical range.

If neither screw adjuster is turned, hinge motion will be unrestricted. If the extension blocking adjuster is screwed in, extension of the hinge will be limited on both arms. If the flexion blocking adjuster is screwed in, flexion of the hinge will be limited on both arms.

The hinge can be locked in any position throughout its range by using one adjuster to place the hinge in the required position and turning the second screw until the hinge locks. Goniometer markings can be provided on the faceplate.

The present invention will now be described in greater detail by way of example only with reference to the accompanying drawings, in which:

FIG. 1 is a front view of the complete hinge mechanism;

FIG. 2. is a sectional front view of the complete hinge mechanism in a first preferred embodiment;

In the following description, the convention of describing components and assemblies in terms of their spatial orientation during use has been followed and for clarity the terms "anterior" and "posterior" have been annotated to several of the drawings.

Figure 1:
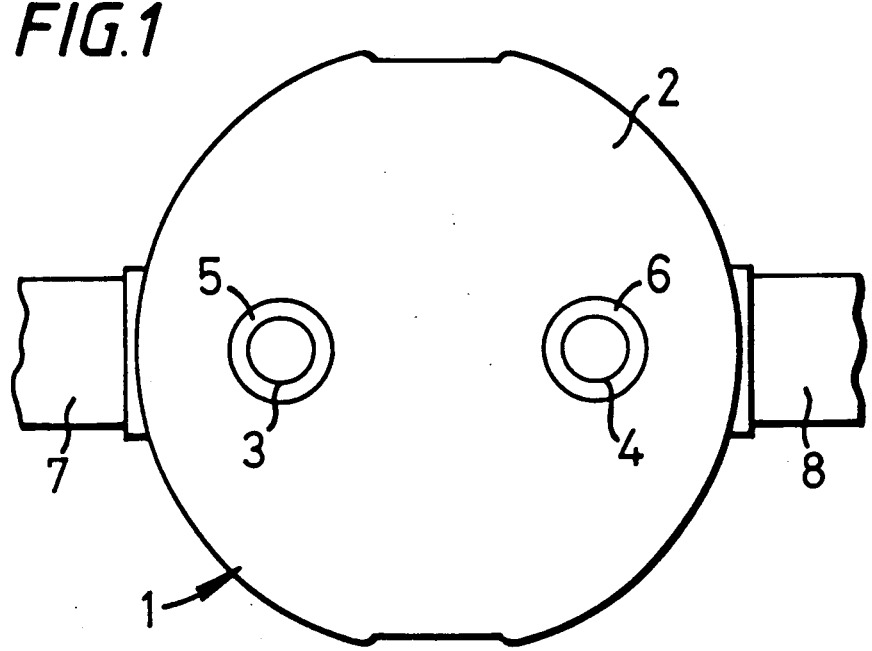

Referring first to FIG. 1 of the drawings, a hinge body 1, is of cast metal or of suitable moulded plastics material. The body includes two parallel plates referred to herein as faceplate 2 and backplate 29. As shown in FIG. 1, faceplate 2 has holes 3 and 4, so sized as to accept inserts 5 and 6 which constitute first and second bearing pivots for hinge arms 7 and 8.

Figure 2:
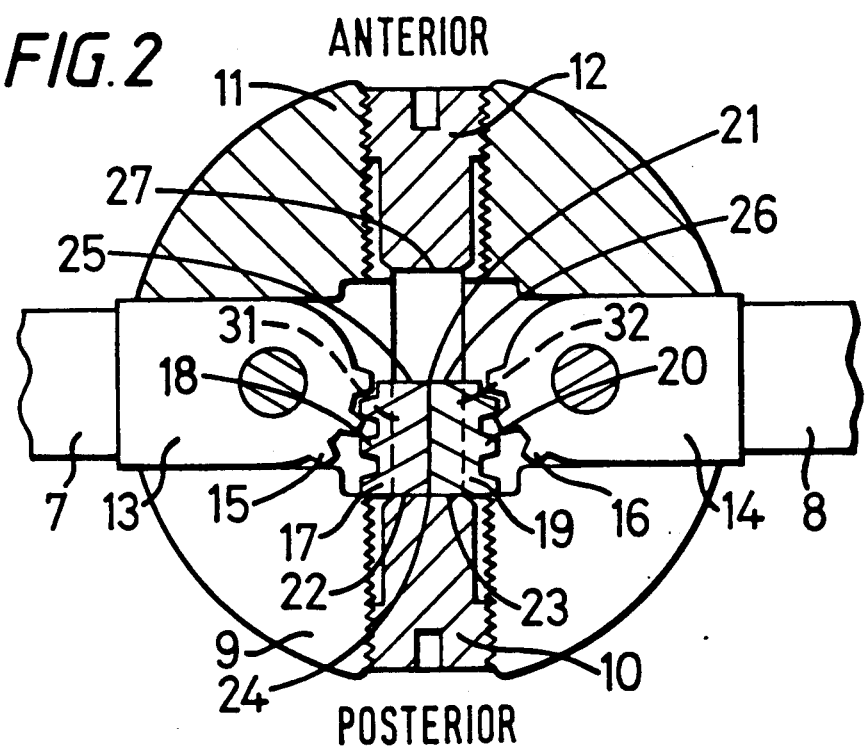

In FIG. 2, a posterior threaded adjuster housing 9 accommodates an adjustment screw 10 and an anterior threaded adjuster housing 11 accommodates an adjustment screw 12. Hinge arm carriers 13 and 14 carry hinge arms 7 and 8 and have toothed peripheries at 15 and 16, respectively.

Toothed slide member 17 has teeth 18 which engage with toothed periphery 15 on hinge arm carrier 13. Toothed slide member 19 has teeth 20 which engage with toothed periphery 16 on hinge arm carrier 14. Toothed slide members 17 and 19 are movable with respect to one another and lie back to back at 21 in hinge body 1. This is to say that slide members 17 and 19 slidably engage one another for independent relative movement, thereby permitting true bi-pivotal motion of hinge arms 7 and 8.

At the limit of extension travel, surfaces 22 and 23 of toothed slide members 17 and 19, respectively, move against the single surface 24 of adjustment screw 10 which forms an extension abutment stop. At the limit of flexion travel, surfaces 25 and 26 of toothed slide members 17 and 19, respectively, move against the single surface 27 of adjustment screw 12 which forms a flexion abutment stop.

It will now be appreciated that because the hinge of the invention has two independent toothed slide members 17 and 19, hinge arms 7 and 8 are not coupled together and thus motion of the device is truly bi-pivotal. However, by providing a single abutment deadstop for flexion and another for extension, adjustment of the limits of travel is very rapid and easy. In the condition shown in FIG. 2, motion of the hinge is unrestricted over its entire range.

Figure 3:
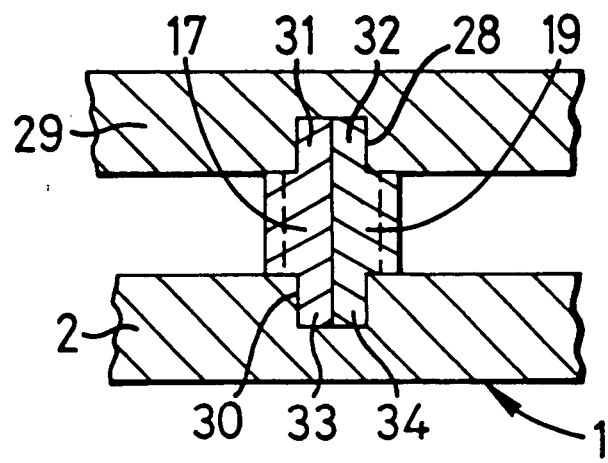
FIG. 3 is a partial sectional overplan view of the toothed slide members located in the hinge body of the first embodiment.

In FIG. 3, toothed slide members 17 and 19 are seen to lie back to back in hinge body 1. Toothed slide members 17 and 19 are retained in groove 28, in backplate 29 and groove 30 in faceplate 2, of hinge body 1, by close fitting lugs 31, 32, 33 and 34. It can also clearly be seen from FIG. 3 that faceplate 2 and backplate 29 are parallel.

Figure 4:
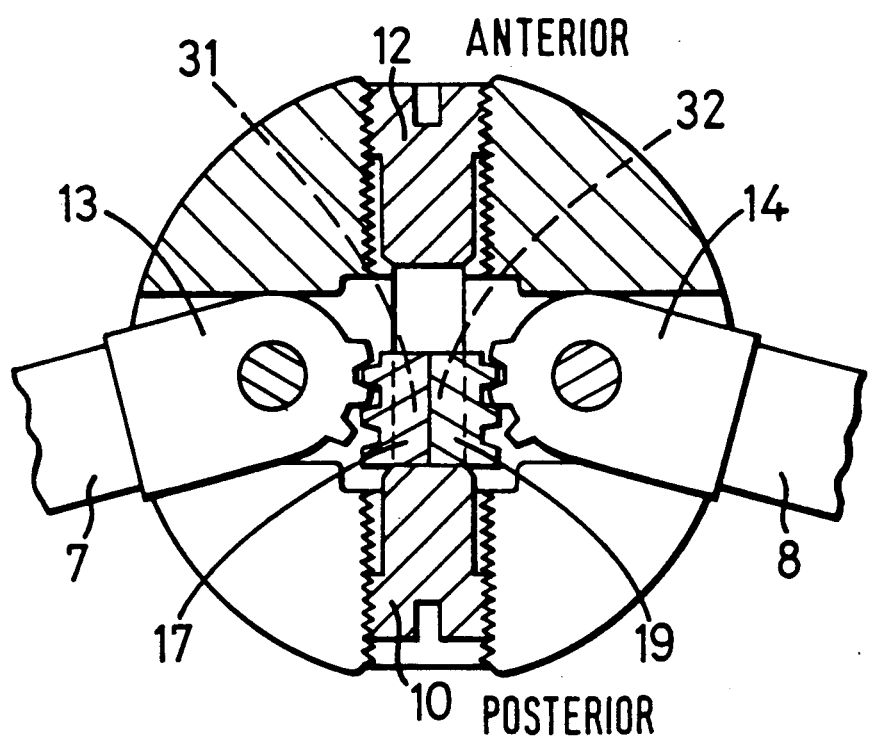
FIG. 4 is a front sectional view of the complete hinge mechanism in the first embodiment showing a restricted range of motion.

Turning to FIG. 4, adjustment screw 10 can be seen to have been screwed partially in. This restricts the posterior motion of toothed slide members 17 and 19 and thus prevents hinge arms 7 and 8 from achieving full extension. This is an essential facility in a hinge which is to be used for post-operative management of anterior cruciate ligament repairs. It will be readily appreciated that this is a true deadstop mechanism.

Figure 5:
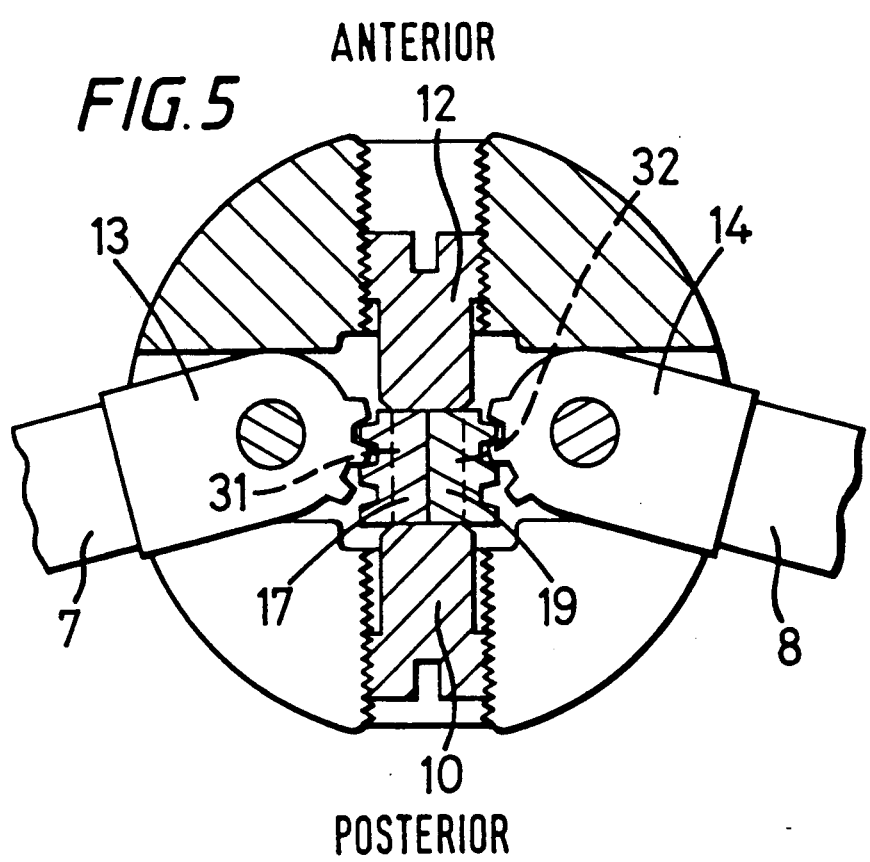
FIG. 5 is a front sectional view of the complete hinge mechanism in the first embodiment showing the hinge locked.

In FIG. 5, adjustment screw 10 can be seen to have been partially screwed in to set up the condition of extension block as described above. Adjustment screw 12 has then also been screwed in until the hinge has locked. This condition is often sought by surgeons in the early post-operative management of anterior cruciate ligament repairs.

Figure 6:
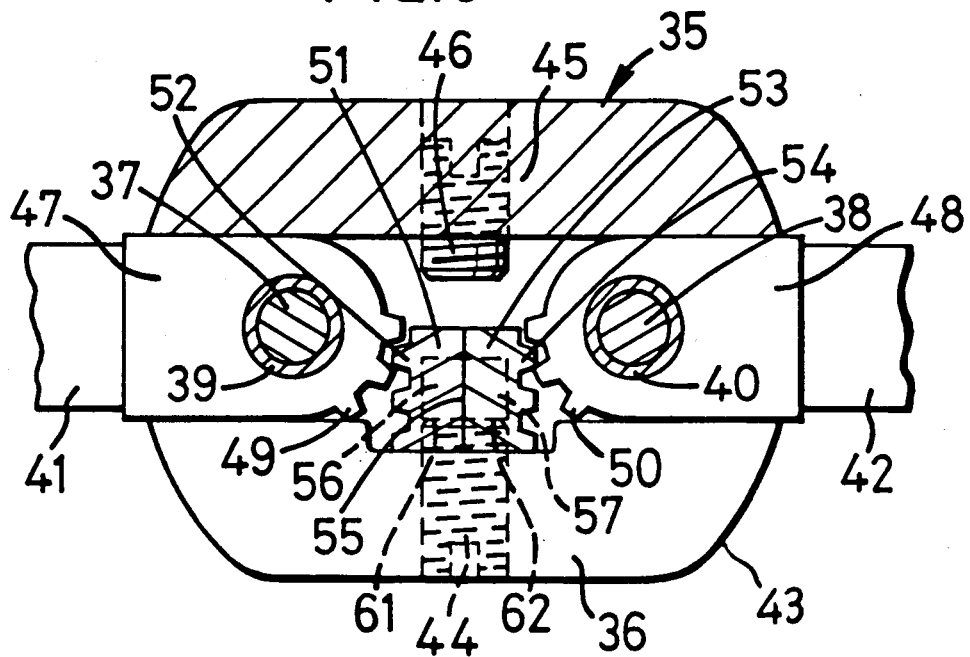
FIG. 6 is a front sectional view of hinge mechanism of a second preferred embodiment.

Turning now to FIG. 6, there is shown a sectional front view of a second preferred embodiment according to the invention. Hinge body 35 is a metal casting or a plastics moulding. Faceplate 36 has holes 37 and 38 so sized as to accept inserts 39 and 40 which constitute first and second bearing pivots for hinge arms 41 and 42. A posterior threaded adjuster housing 43 is positioned within faceplate 36 and accommodates an adjustment screw 44.

An anterior threaded adjuster housing 45 is also positioned within faceplate 36 and accommodates and adjustment screw 46. Hinge arm carriers 47 and 48 carry hinge arms 41 and 42 and have toothed peripheries at 49 and 50, respectively.

Toothed slide member 51 has teeth 52 which engage with toothed periphery 49 on hinge arm carrier 47. Toothed slide member 53 has teeth 54 which engage with toothed periphery 50 on hinge arm carrier 48. Toothed slide members 51 and 53 lie back to back at 55 in hinge body 35. Extensions 56 and 57 protrude into faceplate 36 so as to lie in the paths of adjustment screws 44 and 46 which constitute abutment stops.

Figure 7:
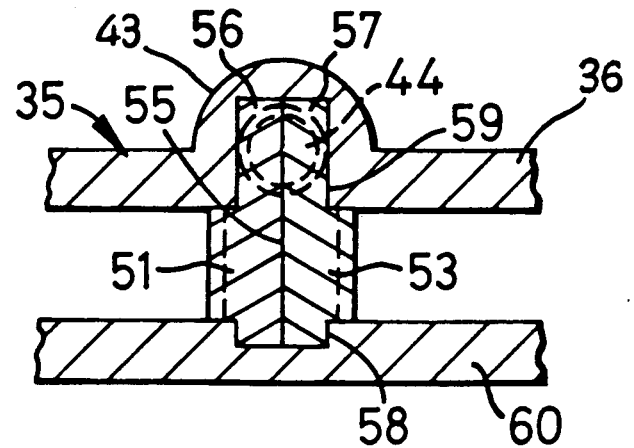
FIG. 7 is a partial sectional overplan view of the toothed slide members located in the hinge body of the second embodiment.

Turning to FIG. 7, which is a sectional overplan view, toothed slide members 51 and 53 are seen to lie back to back at 55 in hinge body 35. Toothed slide members 51 and 53 are retained in hinge body 35 by grooves 58 and 59 in faceplate 36 and backplate 60, respectively. Extensions 56 and 57 lie in the path of adjustment screw 44, shown in hidden detail. It can also be seen that faceplate 36 and backplate 60 are parallel.

Returning to FIG. 6, at the limit of extension travel, surfaces 61 and 62 of extensions 56 and 57, respectively, move against the single surface 63 of adjustment screw 44, which forms an extension abutment stop. At the limit of flexion travel, surfaces 64 and 65 of extensions 56 and 57, respectively, move against the single surface 66 of adjustment screw 46, which forms a flexion abutment stop.

It will be understood that like the first preferred embodiment, this device is truly bi-pivotal and can rapidly and easily be adjusted.

Figure 8:
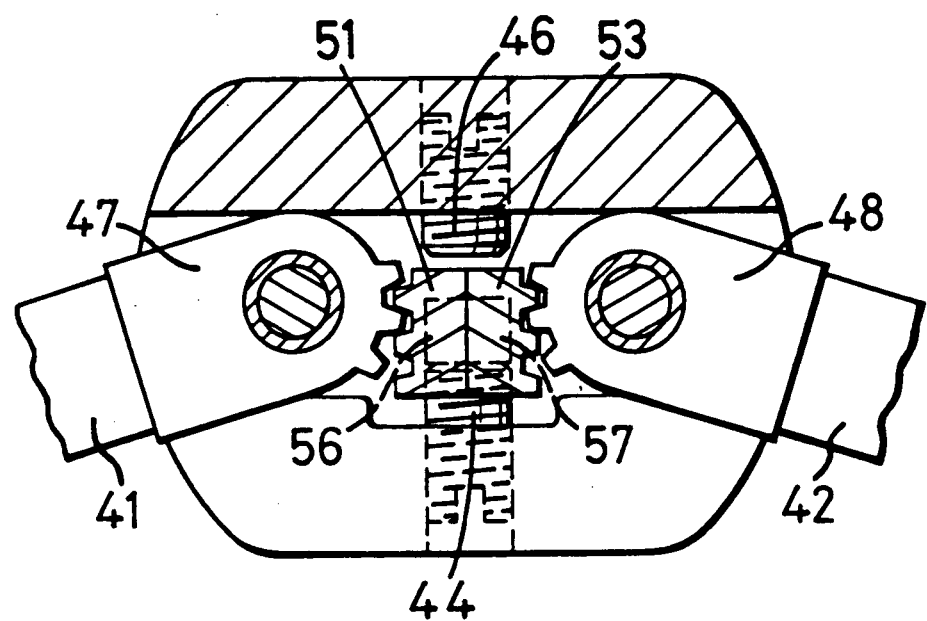
FIG. 8 is a front sectional view of the complete hinge mechanism in the second embodiment showing a restricted range of motion.

For instance, with reference to FIG. 8, adjustment screw 44 can be seen to have been screwed partially in. This restricts the posterior motion of toothed slide members 51 and 53 and thus prevents hinge arms 41 and 42 from achieving full extension.

Figure 9:
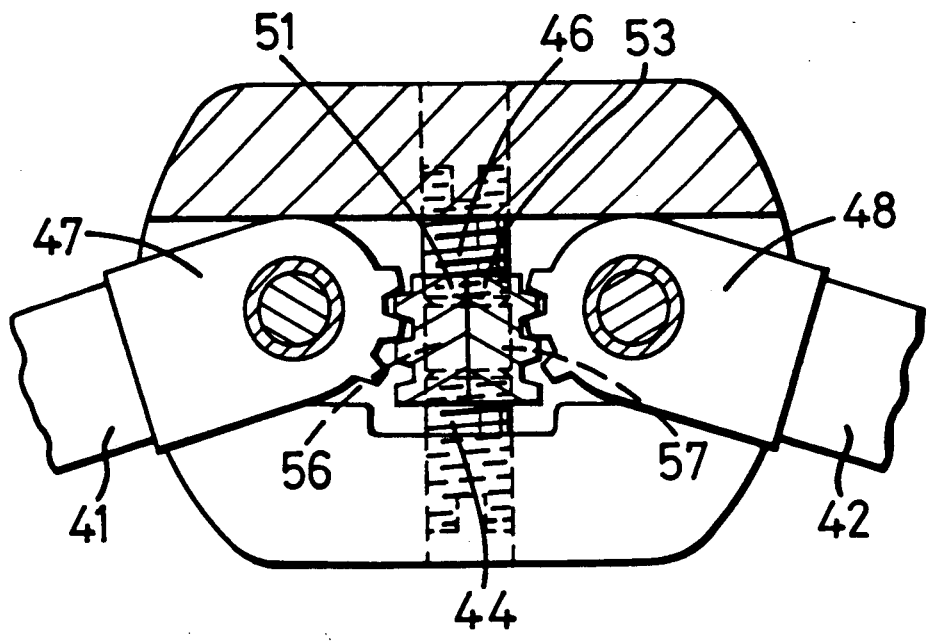
FIG. 9 is a front sectional view of the complete hinge mechanism in the second embodiment showing the hinge locked.

In FIG. 9, adjustment screw 44 can be seen to have partially screwed in to set up the condition of extension block. Adjustment screw 46 has then also been screwed in until the hinge has locked.

This second preferred embodiment can be made smaller and more compact than the first preferred embodiment by virtue of extensions 56 and 57, shown in FIG. 7. Their presence allows the antero-posterior dimension of the hinge to be reduced in the second preferred embodiment since adjustment screws 44 and 46 can travel well past the bottom and top, respectively, of toothed slide members 51 and 53. In the first preferred embodiment, adjustment screws 10 and 12 drive against the bottom and top, respectively, of toothed slide members 17 and 19.

In embodiments which have been made, and as disclosed the hinge body has been comprised of an integral faceplate and backplate (as indicated by the uniform crosshatching in FIGS. 3 and 7), but it is to be understood that such hinge body may, if desired, be made of two or more separate pieces secured together.

We claim:

1. An orthopaedic and orthotic hinge comprising a hinge body including two plates disposed in spaced parallel relationship;
first and second pivot means in the form of axial bearings extending between and in a plane normal to said plates;
first and second hinge arm carriers borne on the axial bearings for pivotal movement in directions of flexion and extension and having peripheral teeth;
first and second toothed slide members, engaging the peripheral teeth of said first and second hinge arm carriers respectively; said slide members being slidably mounted between said plates for independent sliding movement when said hinge arm carriers are pivoted, and said slide members being disposed in sliding contact with each other; and first and second variable stop means for limiting the extent of sliding movement in opposite directions of said first and second slide members and thereby restricting extension and flexion of the hinge arm carriers.

2. A hinge according to claim 1, wherein the slide members are retained for sliding movement within grooves in opposing faces of said parallel plates.

3. A hinge according to claim 1 or claim 2, wherein each variable stop means comprises an adjuster screw threaded in a boss located between said plates in alignment with and on opposite sides of said toothed slide members.

4. A hinge according to claim 3, wherein said plates are integral with each other.

5. A hinge according to claim 3, wherein said adjuster screws are offset with respect to a plane extending between and equidistant from said parallel plates and wherein said toothed slide members are provided with extensions engagable with said offset adjuster screws.

6. A hinge according to claim 5, wherein said boss is integral with one of said plates.

7. A hinge according to claim 6, wherein said plates are integral with each other.

* * * * *